(12) United States Patent
Liechty et al.

(10) Patent No.: US 11,298,309 B2
(45) Date of Patent: Apr. 12, 2022

(54) TOPICAL SILK COMPOSITIONS AND METHODS OF USING

(71) Applicants: THE REGENTS OF THE UNIVERSITY OF COLORADO, Denver, CO (US); UNIVERSITY OF CENTRAL FLORIDA RESEARCH FOUNDATION, INC., Orlando, FL (US)

(72) Inventors: Ken Liechty, Aurora, CO (US); Sudipta Seal, Orlando, FL (US); Swetha Barkam, Boise, ID (US)

(73) Assignees: THE REGENTS OF THE UNIVERSITY OF COLORADO, Denver, CO (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 16/641,606

(22) PCT Filed: Aug. 24, 2018

(86) PCT No.: PCT/US2018/047914
§ 371 (c)(1),
(2) Date: Feb. 24, 2020

(87) PCT Pub. No.: WO2019/040850
PCT Pub. Date: Feb. 28, 2019

(65) Prior Publication Data
US 2021/0030656 A1 Feb. 4, 2021

Related U.S. Application Data

(60) Provisional application No. 62/549,579, filed on Aug. 24, 2017.

(51) Int. Cl.
| | | |
|---|---|---|
| A61K 8/64 | (2006.01) |
| A61K 47/69 | (2017.01) |
| A61K 47/54 | (2017.01) |
| A61P 17/02 | (2006.01) |
| A61K 33/244 | (2019.01) |
| A61K 8/02 | (2006.01) |
| A61K 8/19 | (2006.01) |
| A61K 8/98 | (2006.01) |
| A61K 9/00 | (2006.01) |
| A61K 9/08 | (2006.01) |
| A61K 9/70 | (2006.01) |
| A61K 35/28 | (2015.01) |
| A61K 35/64 | (2015.01) |
| A61K 35/646 | (2015.01) |
| A61K 38/17 | (2006.01) |
| A61Q 19/00 | (2006.01) |
| C12N 15/113 | (2010.01) |

(52) U.S. Cl.
CPC ............... *A61K 8/64* (2013.01); *A61K 8/027* (2013.01); *A61K 8/19* (2013.01); *A61K 8/987* (2013.01); *A61K 9/0014* (2013.01); *A61K 9/08* (2013.01); *A61K 9/7007* (2013.01); *A61K 9/7015* (2013.01); *A61K 33/244* (2019.01); *A61K 35/28* (2013.01); *A61K 35/64* (2013.01); *A61K 35/646* (2013.01); *A61K 38/1767* (2013.01); *A61K 47/549* (2017.08); *A61K 47/6923* (2017.08); *A61P 17/02* (2018.01); *A61Q 19/00* (2013.01); *C12N 15/113* (2013.01); *A61K 2800/30* (2013.01); *C12N 2310/141* (2013.01); *C12N 2310/351* (2013.01)

(58) Field of Classification Search
CPC .... A61K 8/64; A61K 47/6923; A61K 47/549; A61K 33/244; A61K 8/027; A61K 8/19; A61K 8/987; A61K 9/0014; A61K 9/08; A61K 9/7007; A61K 9/7015; A61K 35/28; A61K 35/64; A61K 35/646; A61K 38/1767; A61K 2800/30; A61K 47/10; A61K 47/46; A61K 38/12; A61K 8/981; A61P 17/02; A61Q 19/00; C12N 15/113; C12N 2310/141; C12N 2310/351; A61L 15/32

See application file for complete search history.

(56) References Cited

U.S. PATENT DOCUMENTS

| | | |
|---|---|---|
| 3,247,845 A | 4/1966 | Kennedy |
| 2011/0111031 A1 | 5/2011 | Jiang et al. |
| 2016/0193293 A1 | 7/2016 | Nishi et al. |

FOREIGN PATENT DOCUMENTS

WO 2017/091700 6/2017

OTHER PUBLICATIONS

PCT, "International Search Report and Written Opinion", Application No. PCT/US2018/047914, dated Oct. 25, 2018, 13 pages.
Zgheib et al., "Silk Fibroin Improves the Biomechanical Properties of Diabetic Skin", Wound Repair and Regeneration, vol. 23, 2015, pp. A14, A47.

*Primary Examiner* — Robert S Cabral
(74) *Attorney, Agent, or Firm* — Dorsey & Whitney LLP

(57) ABSTRACT

Methods of protecting skin of a mammal by application of silk-derived compositions useful for treating or preventing a wide variety of skin conditions. Silk solutions and silk mats are prepared and applied to the skin surface. The silk compositions may be self-adhesive or sutured to cover a wound or area of skin exposed to physical stresses and strains, thereby preventing a wound and/or promoting wound healing.

13 Claims, 4 Drawing Sheets

TOPICAL SILK COMPOSITIONS AND METHODS OF USING

CROSS REFERENCE TO RELATED APPLICATION

This application is a national stage application under 35 U.S.C. § 371 of International Application No. PCT/US2018/047914, filed Aug. 24, 2018, entitled "TOPICAL SILK COMPOSITIONS AND METHODS OF USING," which claims the benefit of U.S. Provisional Patent Application Ser. No. 62/549,579, filed Aug. 24, 2017, the entire disclosures of which are hereby incorporated herein by reference.

TECHNICAL FIELD

The present invention relates to silk fibroin-based materials, processes of making the same, and uses of the same.

BACKGROUND

Silks are protein polymers that are spun into fibers by some lepidoptera larvae such as silkworms, spiders, scorpions, mites and flies. Silk proteins are usually produced within specialized glands after biosynthesis in epithelial cells, followed by secretion into the lumen of these glands where the proteins are stored prior to spinning into fibers. Silks differ widely in composition, structure and properties depending on the specific source. The most extensively characterized silks are from the domesticated silkworm, *Bombyx mori*, and from spiders (*Nephila clavipes* and *Araneus diadematus*). Many spiders synthesize different types of silks. Each of these different silks has a different amino acid composition and exhibits mechanical properties tailored to their specific functions: reproduction as cocoon capsular structures, lines for prey capture, lifeline support (dragline), web construction and adhesion.

The major components of silk are fibroin and sericin. Fibroin is a fibrous protein constituting the core of silk, while sericin is a glue-like protein surrounding fibroin. Fibroin has been traditionally processed to threads for surgical suture because it is available in bulk at an industrial scale, shows no toxicity, and is biocompatible with human tissues. Fibroin solution is convertible to various forms such as films, sponge, gel, and powder.

It is desirable to tune the mechanical properties of silk compositions to produce silk fibroin materials that are biocompatible and provide enhanced mechanical strength to biological structures.

SUMMARY

There is an unmet need for biocompatible and hypoallergenic compositions that can protect skin and other biological structures from mechanical stresses and injuries.

The present inventors have discovered that a layered system of silk fibroin in solution and spun mat formats can be applied to skin to effectively protect and strengthen skin where needed in areas of weakness or areas subject to injuries or repetitive stresses.

Thus, this disclosure provides a method of protecting the skin of a mammal by applying a solution of silk fibroin fibers to the skin, and applying a silk fibroin mat over the silk solution, thereby increasing the elastic modulus of the skin of the mammal. In these methods, the silk fibroin fibers in the solution may have a diameter in the range from 1 nm to 1,000 nm. The silk fibroin fibers in the solution may be obtained from a solution containing a dissolved silkworm silk, such as silk obtained from *Bombyx mori*. The silk fibroin fibers may be obtained from a solution containing a dissolved spider silk, such as spider silk obtained from *Nephila clavipes*. The silk fibroin fibers in the solution may be treated to have a sericin content of less than 5%, for example silk fibroin fibers in the solution may be substantially free of sericin. The silk fibroin fibers in the solution may have a concentration of about 0.1 to about 25 weight percent of the solution. The solution of silk fibroin fibers may be an aqueous solution, including an alcohol solution.

In these methods, the solution of silk fibroin fibers may further comprise a biocompatible polymer selected from the group comprising polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, and combinations thereof.

The solution of silk fibroin fibers may be applied as at least one of a spray, a liquid, a film, a foam, a suspension, a cream, an ointment, or a gel.

The silk fibroin fibers in the silk fibroin mat may have a diameter in the range from 1 nm to 1,000 nm. The silk fibroin fibers in the silk fibroin mat may be obtained from a solution containing a dissolved silkworm silk such as silkworm silk is obtained from *Bombyx mori*. The silk fibroin fibers in the silk fibroin mat may be obtained from a solution containing a dissolved spider silk, such as spider silk obtained from *Nephila clavipes*. The silk fibroin fibers in the silk fibroin mat may have a sericin content of less than 5%, for example the silk fibroin fibers in the silk fibroin mat are substantially free of sericin.

In these methods, the silk fibroin mat may further comprise a biocompatible polymer selected from the group comprising polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, and combinations thereof.

The silk fibroin mat may be applied as at least one of a sheet, a gel, a hydrogel, a mesh, a non-woven mat, a fabric, a scaffold, a tube, a slab, a fiber, a particle, a powder, a sponge, and a lyophilized article.

The silk fibroin mat may be formed from a composition of silk fibers by a process selected from gel spinning, lyophilization, casting, molding, electrospinning, machining, wet-spinning, dry-spinning, milling, spraying, phase separation, template-assisted assembly, rolling, compaction, and any combinations thereof.

The silk fibroin mat may further comprise a layer of an adhesive disposed on at least one surface of the mat.

In these methods, the mammal is preferably a human. The mammal may be a diabetic mammal, particularly a diabetic human. The mammal may be an elderly mammal.

This disclosure also provides a method of protecting an area of the skin from chaffing or from the formation of blisters by applying a solution of silk fibroin fibers to an area of skin of a mammal that is to be protected, and applying a silk fibroin mat over the silk solution to the skin of the mammal such that the area of skin is covered by a protective layer of silk fibroin fibers, thereby increasing the elastic modulus of the skin of the mammal and minimizing any external friction forces to the area of skin to be protected.

This disclosure also provides a method of treating a blister by applying a solution of silk fibroin fibers to the site of a blister formed on the skin of a mammal, and applying a silk fibroin mat over the silk solution to the skin of the mammal such that the blister is covered by a protective layer of silk fibroin fibers, thereby increasing the biomechanical strength of the skin of the mammal and minimizing any external friction forces to the blister.

This disclosure also provides a method of preventing injury to an area of the skin by applying a solution of silk fibroin fibers to an area of skin of a mammal that is susceptible to injury, and applying a silk fibroin mat over the silk solution to the skin of the mammal such that the area of skin is covered by a protective layer of silk fibroin fibers, thereby increasing the elastic modulus of the skin to prevent or substantially reduce injury of the area of skin covered by the protective layer of silk fibroin fibers.

This disclosure also provides a method of treating a wound by topically administering to a mammal in need of such therapy a solution of silk fibroin fibers incorporating an active agent that is effective in enhancing the healing of the wound and/or reducing the time to heal. In these methods, a silk fibroin mat may be applied over the silk solution to enhanced the healing of the wound. The silk fibroin mat may comprise an active agent that is effective in enhancing the healing of the wound and/or reducing the time to heal. The active agent may be a cerium oxide nanoparticle comprising a miR, which may be miR-146a.

This disclosure also provides a cosmetic or dermatological composition comprising a silk fibroin solution and at least one cosmetic adjuvant. The cosmetic adjuvant is selected from fatty substances, glycosaminoglycans, extracellular matrix molecules, organic solvents, ionic and nonionic thickeners, softeners, antioxidants, free-radical scavengers, opacifiers, stabilizers, emollients, silicones, alphahydroxy acids, insect repellents, antifoams, moisturizers, vitamins, fragrances, preserving agents, surfactants, fillers, polymers, propellants, acidifying and basifying agents, and colorants. The cosmetic or dermatological composition may further comprise a cerium oxide nanoparticle comprising a miR, which may be miR-146a.

This Summary is neither intended nor should it be construed as representative of the full extent and scope of the present disclosure. Moreover, references made herein to "the present disclosure," or aspects thereof, should be understood to mean certain embodiments of the present disclosure and should not necessarily be construed as limiting all embodiments to a particular description. Additional aspects of the technology will become readily apparent from the Description of Embodiments, particularly when taken together with the figures.

BRIEF DESCRIPTION OF THE DRAWINGS

The following drawings form part of the present disclosure and are included to further demonstrate certain aspects of the present technology. The embodiments may be better understood by reference to one or more of these drawings in combination with the detailed description presented herein.

FIG. 3 shows a graph of percent of original wound area versus time post-wounding in diabetic mice showing effect of CNP and CNP-miR146a.

DESCRIPTION OF EMBODIMENTS

Figure 1:
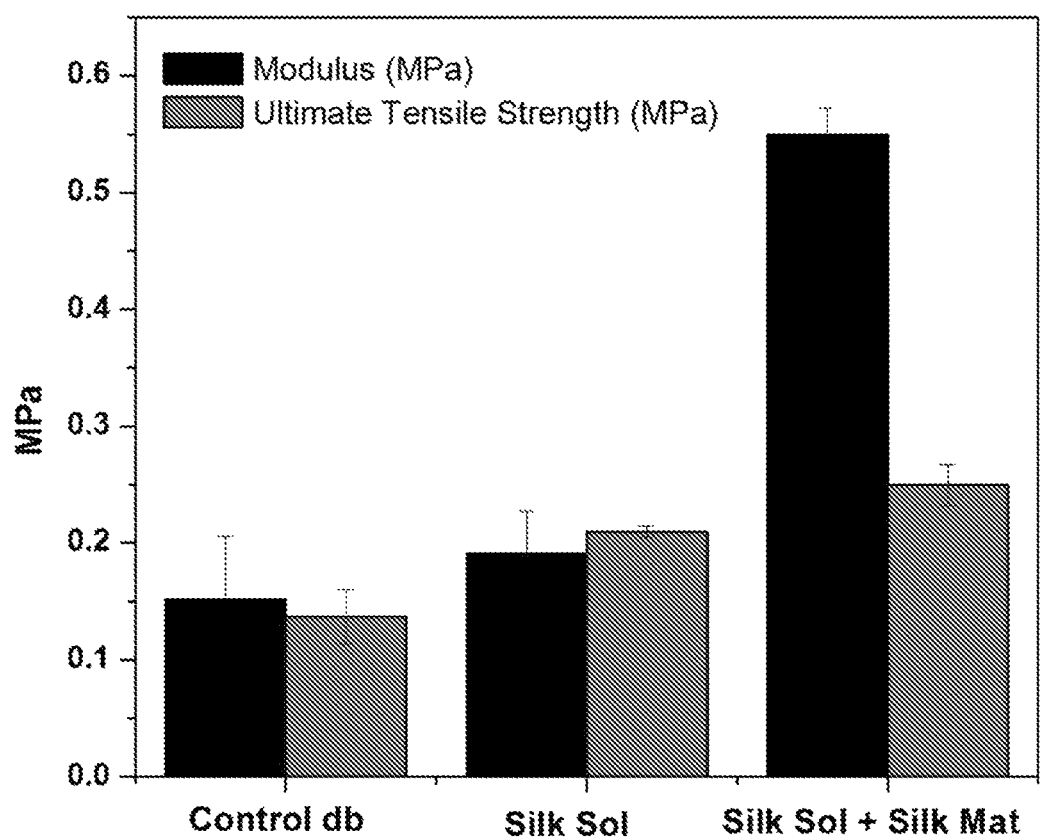
FIG. 1 shows the effect of treating mammalian skin with silk fibroin solution, or silk fibroin and silk fibroin mat on elastic modulus of the skin.

The present disclosure is drawn to methods of using silk fibroin compositions and layers to protect and strengthen skin of a mammal.

The unique mechanical properties of reprocessed silk such as fibroin and its biocompatibility make the silk fibers especially attractive for use in biotechnological materials and medical applications. Silk provides an important set of material options for biomaterials and tissue engineering because of the impressive mechanical properties, biocompatibility and biodegradability (Altman, G. H., et al., Biomaterials 2003, 24, 401-416; Cappello, J., et al., J. Control. Release 1998, 53, 105-117; Foo, C. W. P., et al., Adv. Drug Deliver. Rev. 2002, 54, 1131-1143; Dinerman, A. A., et al., J. Control. Release 2002, 82, 277-287; Megeed, Z., et al., Adv. Drug Deliver. Rev. 2002, 54, 1075-1091; Petrini, P., et al., J. Mater. Sci-Mater. M. 2001, 12, 849-853; Altman, G. H., et al., Biomaterials 2002, 23, 4131-4141; Panilaitis, B., et al., Biomaterials 2003, 24, 3079-3085).

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

The term "a plurality of" as used herein refers to 2 or more, including, e.g., 3 or more, 4 or more, 5 or more, 6 or more, 7 or more, 8 or more, 9 or more, 10 or more, 20 or more, 30 or more, 40 or more, 50 or more, 100 or more, 500 or more, 1000 or more, 5000 or more, or 10000 or more.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "statistically significant" or "significantly" refers to statistical significance and generally means at least two standard deviations away from a reference level. The term refers to statistical evidence that there is a difference. It is defined as the probability of making a decision to reject the null hypothesis when the null hypothesis is actually true.

As used interchangeably herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

As used herein, the phrase "silk fibroin solution" or "silk fibroin mat" refers to a material in which the silk fibroin constitutes at least about 10% of the total material, including at least about 20%, at least about 30%, at least about 40%, at least about 50%, at least about 60%, at least about 70%, at least about 80%, at least about 90%, at least about 95%, up to and including 100% or any percentages between about 30% and about 100%, of the total material. In certain embodiments, the silk fibroin-based compositions can be substantially formed from silk fibroin. The silk fibroin-based materials can be substantially formed from silk fibroin. Where the silk fibroin constitutes less than 100% of the total compositions, the silk fibroin-based material can comprise a different material and/or component including, but not limited to, a metal, a synthetic polymer, e.g., but not limited to, polyethylene glycol (PEG), poly(vinyl alcohol) and poly (vinyl pyrrolidone), a hydrogel, an active agent, an additive described herein, and any combinations thereof. As used herein, the terms "a dissolved silk" and "a silk solution" are interchangeably.

Silk Fibroin Solution

Silk fibroin is a particularly appealing protein polymer candidate for use in various embodiments described herein, e.g., because of its versatile processing e.g., all-aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)).

Silk fibroin includes silkworm fibroin and insect or spider silk protein. See e.g., Lucas et al., 13 Adv. Protein Chem. 107 (1958). Any type of silk fibroin can be used according to aspects of the present invention. Silk fibroin produced by silkworms, such as *Bombyx mori*, is the most common and represents an earth-friendly, renewable resource. For instance, silk fibroin can be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks (recombinant silk), such as silks from bacteria, yeast, mammalian cells, transgenic animals, or transgenic plants, and variants thereof, that can be used. See for example, WO 97/08315 and U.S. Pat. No. 5,245,012, content of both of which is incorporated herein by reference in its entirety. In some embodiments, silk fibroin can be derived from other sources such as spiders, other silkworms, bees, and bioengineered variants thereof. In some embodiments, silk fibroin can be extracted from a gland of silkworm or transgenic silkworms. See for example, WO2007/098951, content of which is incorporated herein by reference in its entirety. In some embodiments, silk fibroin is free, or essentially free of sericin, i.e., silk fibroin is a substantially sericin-depleted silk fibroin.

The silk fibroin compositions contain at least one silk protein, including fibroin, fibroin-related protein, or modified fibroin protein. The silk protein in these compositions may range from about 10% (w/w) to about 100% (w/w), from about 20% (w/w) to about 95% (w/w), from about 30% (w/w) to about 90% (w/w), from about 40% (w/w) to about 85% (w/w), from about 50% (w/w) to about 80% (w/w), from about 60% (w/w) to about 99% (w/w), from about 70% (w/w) to about 99% (w/w), from about 80% (w/w) to about 99% (w/w), from about 80% (w/w) to about 100% (w/w), from about 90% (w/w) to about 99% (w/w), or from about 80% (w/w) to about 90% (w/w). Higher or lower silk protein content may also be possible.

The water content in the present compositions may range from about 0% (w/w) to about 60% (w/w), from about 0.5% (w/w) to about 50% (w/w), from about 1% (w/w) to about 40% (w/w), from about 1% (w/w) to about 30% (w/w), from about 1% (w/w) to about 20% (w/w), from about 1% (w/w) to about 15% (w/w), from about 1% (w/w) to about 12% (w/w), from about 2% (w/w) to about 10% (w/w), from about 3% (w/w) to about 9% (w/w), from about 4% (w/w) to about 8% (w/w), from about 5% (w/w) to about 7% (w/w), from about 6% (w/w) to about 12% (w/w), from about 5% (w/w) to about 10% (w/w), or from about 5% (w/w) to about 15% (w/w). Higher or lower water content may also be possible.

The present compositions contain at least one silk protein or peptide, which may be fibroin or related proteins, or fragments or variants thereof. Fibroin can be obtained from a solution containing a dissolved silk. Silk can be a silkworm silk, e.g., from domesticated silkworm *Bombyx mori*, a spider silk, e.g. from *Nephila clavipes*. Other sources of silk include, but are not limited to, other strains of Bombycidae including *Antheraea pernyi, Antheraea yamamai, Antheraea mylitta, Antheraea assama*, and *Philosamia cynthia ricini*, as well as silk producing members of the families Saturnidae, Thaumetopoeidae. Lucas et al., Adv. Protein Chem. 13: 107-242 (1958). In general, silks can be produced by certain species in the class Insecta, including the order Lepidoptera (butterflies), and by species in the class Arachnida, including the order Araneae (spiders).

The starting material for fibroin may be cocoons, cocoon filaments, raw silk, silk fabrics, silk yarn, degummed silk, any other partially cleaned silk, etc. This may also include short fragments of raw or sericin-depleted silk. Silks may also be obtained from a recombinant source, such as silks from genetically engineered cells (e.g., bacteria, yeast, insect or mammalian cells), silks from transgenic plants and animals, silks from cultured cells, silks from cloned full or partial sequences of native silk genes, and silks from synthetic genes encoding silk or silk-like sequences. See, for example, WO 97/08315 and U.S. Pat. No. 5,245,012.

In certain embodiments, the silk used for generation of the present compositions is substantially depleted of its sericin content (i.e., less than about 4% (w/w) residual sericin in the final extracted silk). Alternatively, higher concentrations of residual sericin may be left on the silk following extraction or the extraction step may be omitted. In aspects of this embodiment, the sericin-depleted silk fibroin has, e.g., less than about 1% (w/w), less than about 2% (w/w), less than about 3% (w/w), less than about 4% (w/w), less than about 5% (w/w), less than about 10% (w/w), less than about 15% (w/w), about 1% (w/w) to about 2% (w/w), about 1% (w/w) to about 3% (w/w), or about 1% (w/w) to about 4% (w/w) residual sericin.

As used herein, the term "degumming" refers to heating silk cocoons in an aqueous solution to remove at least a portion of sericin from the silk. Degumming may include heating silk cocoons in an aqueous solution to substantially remove sericin from native silk fibers. For example, the degummed silk fibers can have a sericin content of less than 10%, less than 8%, less than 6%, less than 5%, less than 4%, less than 3%, less than 2%, less than 1% or lower. In some embodiments, the degummed silk fibers can have a sericin content of less than 5% or lower.

Sericin may also be removed from silk through the use of reagents including, but are not limited to, urea solutions, hot water, enzyme solutions (e.g., papain, etc.). Mechanical methods may also be used to remove sericin from silk fibroin, including, ultrasound, abrasive scrubbing, and fluid flow. For example, to remove sericin, B. mori cocoons may be boiled in an aqueous solution, for example, for about 10 minutes to about 5 hours. Shorter or longer boiling time periods are also possible. The aqueous solution can be any suitable solution facilitating the removal of sericin, such as sodium bicarbonate in the concentration of about 0.02M. The cocoons may be rinsed with water to extract the sericin proteins.

After sericin is removed, the resulting silk can be solubilized using a dissolution agent (e.g., a chaotropic agent) to produce a dissolved silk containing fibroin. The dissolution agent may be an aqueous salt solution. Salts useful for this purpose include, but are not limited to, lithium bromide, lithium thiocyanate, calcium nitrate, calcium chloride, cupriethylenediamine, sodium thiocyanate, lithium thiocyanate, magnesium nitrate or other magnesium salts, zinc chloride, sodium thiocyanate, other lithium and calcium halides, other ionic species, urea or other chemicals capable of solubilizing silk. For example, the extracted silk may be dissolved in 9M to 12 M LiBr solution. The dissolution agent can be in any suitable solvent, including, but not limited to, aqueous solutions, alcohol solutions, 1,1,1,3,3,3-hexafluoro-2-propanol, hexafluoroacetone, and 1-butyl-3-methylimidazolium. These solvents may also be modified through adjustment of pH by addition of acidic of basic compounds.

When the dissolution agent contains a salt, the salt may subsequently be removed by dialysis. The silk solution may be dialyzed in water for about 2 hours to about 72 hours, or about 6 hours to about 48 hours. For example, a dialysis cassette or tubing with a molecular weight cutoff of 3500 Da may be used. Shorter or longer dialysis time periods are also possible. The dialysis membrane may be cellulose membranes or any other semi-permeable membrane. Any suitable dialysis system may be used.

Dissolution agents may also be organic solvents. Such methods have been described in, Li et al., J. Appl. Poly Sci. 2001, 79, 2192-2199; Min, et al. Sen'l Gakkaishi 1997, 54, 85-92; Nazarov et al., Biomacromolecules 2004 May-June; 5(3):718-26. U.S. Pat. No. 8,178,656. The dissolution agent may alternatively be an acid solution (e.g., formic acid, hydrochloric acid, etc.). An exemplary organic solvent that can be used to produce a silk solution includes, but is not limited to, hexafluoroisopropanol (HFIP). See, for example, International Application No. WO2004/000915, content of which is incorporated herein by reference in its entirety.

During the dissolution process, various parameters may be modified, including, but not limited to, solvent type, silk concentration, temperature, pressure, and addition of mechanical disruptive forces. Mechanical mixing methods employed may also vary, including, for example, agitation, mixing, and sonication.

If necessary, the silk solution may be concentrated by dialyzing against a hygroscopic polymer, for example, polyethylene glycol (PEG), polyethylene oxide, or amylose. The PEG may be of a molecular weight of 8,000-10,000 g/mol and has a concentration of 25-50%. The dialysis may be about 2 hours to about 12 hours. See, for example, PCT application PCT/US/04/11199. It is also possible to change the buffer phase in the dialysis system, altering water purity or adding hygroscopic polymers to simultaneously remove ions and water from the initial silk solution.

Insoluble debris may be removed from the silk solution at any stage by centrifugation or filtration.

The resultant dissolved silk may have a silk protein (e.g., fibroin) concentration ranging from about 1% (w/v) to about 50% (w/v). It may be possible to expand this range to include higher or lower fractions of dissolved silk.

In some embodiments, the silk fibroin solution can be further processed to isolate silk fibroin having a specific high molecular weight, or within a specific high molecular weight distribution. Methods for purifying polymers with a desirable molecular weight or a molecular weight distribution are known in the art, e.g., but not limited to, gel permeation chromatography, and can be used to isolate silk fibroin with a specific molecular weight or molecular weight distribution. Thus, the resulting silk fibroin solutions may include or be composed of a high molecular weight (MW) silk fibroin which generally has longer protein chains. As used herein, the term "high molecular weight (MW) silk fibroin" refers to silk fibroin proteins having an average molecular weight of at least about 100 kDa or more, including, e.g., at least about 150 kDa, at least about 200 kDa, at least about 250 kDa, at least about 300 kDa, at least about 350 kDa or more. In some embodiments, the silk fibroin proteins can have an average molecular weight of at least about 200 kDa or more. The average molecular weight can be determined from a molecular weight distribution. The molecular weights of silk fibroin proteins can be described by a molecular weight distribution with an average molecular weight defined herein, for example, of at least about 100 kDa or more, including about 150 kDa, at least about 200 kDa or more. The molecular weights of silk fibroin proteins can be described by a molecular weight distribution with an average molecular weight of at least about 200 kDa or more. In these embodiments where silk fibroin has a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

All of the silk fibroin proteins in these solutions may have substantially the same molecular weight as the average molecular weight defined herein (e.g., of at least about 100 kDa). The molecular weights of silk fibroin can be generally measured by any methods known in the art, e.g., but not limited to, gel electrophoresis, gel permeation chromatography, light scattering, and/or mass spectrometry.

In some embodiments, the average molecular weight of silk fibroin can refer to the number average molecular weight of silk fibroin, which is the arithmetic mean or average of the molecular weights of individual silk fibroin proteins.

The molecular weights of the silk fibroin defined herein refers to molecular weights of silk fibroin in a solution as measured by gel electrophoresis, e.g., sodium dodecyl sulfate (SDS)-polyacrylamide gel electrophoresis (PAGE). One of skill in the art will readily appreciate that electrophoretic mobility can be influenced by, e.g., protein folding and/or molecular weight.

Removal of sericin from native silk fibers is desirable due to its implication in inflammatory responses in vivo. Accordingly, the term "substantially free of sericin" can refer to an amount of sericin that does not substantially implicate any inflammatory response in vivo. Examples of an inflammatory response induced by sericin can include, but not limited to, increased production of interleukin (IL)-1 beta and/or tumor necrosis factor (TNF)-alpha by immune cells such as macrophages and monocytes. See, e.g., Aramwit et al., J. Biosci Bioeng. 2009; 107:556-561; Panilaitis B., Biomaterials, 2003. 24:3079-3085.

High molecular weight silk fibroin can be used at any concentrations in a silk fibroin composition of this disclosure, depending on desirable material properties in different applications. In some embodiments, high molecular weight silk fibroin can be present in the silk fibroin composition or silk fibroin article in an amount of about less than 1 wt % to about 50 wt %, about 0.25 wt % to about 30 wt %, about 0.5 wt % to about 15 wt %, or about 0.5 wt % to about 10 wt %, of the total weight or total volume. In some embodiments, silk fibroin can be present in the silk fibroin composition or silk fibroin article in an amount of about less than 1 wt % to about 20 wt % or higher, about 0.25 wt % to about 15 wt %, or about 0.5 wt % to about 10 wt %, of the total weight or volume. In some embodiments, high molecular weight silk fibroin can be present in the silk fibroin composition or silk fibroin article in an amount of about 5 wt % to about 50 wt %, about 10 wt % to about 40 wt %, about 20 wt % to about 30 wt %, of the total weight or volume.

High molecular weight silk fibroin can be used at a low concentration (e.g., in a range of about 5% w/v to as low as 0.5% w/v silk fibroin solution) to form a mechanically stable (e.g., ability to maintain shape and/or volume) silk fibroin composition or silk fibroin scaffold of this disclosure. As used herein, the term "mechanically stable" refers to an ability of a silk-based composition to maintain shape and/or volume after physical manipulation, e.g., during silk processing, handling, and/or application (e.g., topical application). The term "maintain shape and/or volume" refers to no substantial change in shape and/or volume of a silk fibroin-based material, or alternatively, the change in shape and/or volume of a silk fibroin-based material being less than 30% or lower (including, e.g., less than 20%, less than 10% or lower), after physical manipulation, e.g., during silk processing, handling, and/or application (e.g., implantation). In some embodiments, a mechanically-stable silk fibroin-based composition can deform under loading but restore to its original shape and/or shape (e.g., restore to at least about 50% or more, including, for example, at least about 60%, at least about 70%, at least about 80%, at least about 90%, at least about 95% or more, of its original shape and/or shape) after release of the loading.

Accordingly, another aspect provided herein relates to a composition comprising a mechanically-stable silk fibroin composition comprising a low concentration of silk fibroin. The mechanically-stable silk fibroin composition or silk fibroin article may comprise a low concentration of high molecular weight silk fibroin. As used herein, the term "low concentration of silk fibroin" can refer to a mass concentration of silk fibroin (e.g., high molecular weight silk fibroin) present in a silk fibroin composition, at or below which high molecular weight silk fibroin, but not relatively low molecular weight silk fibroin (e.g., silk fibroin produced by a process involving a typical degumming process, can form a mechanically-stable structure. The term "low concentration of silk fibroin" can refer to a mass concentration of silk fibroin (e.g., high molecular weight silk fibroin) present in a silk fibroin composition, at or below which the resulting mechanically-stable structure can degrade in vivo, or in the presence of a protease or silk-degrading enzyme, at a rate at least comparable to or faster than the degradation rate of a silk fibroin composition formed from relatively low molecular weight silk fibroin at a minimum concentration required to yield a mechanically-stable structure. In some embodiments, the term "low concentration of silk fibroin" can refer to a mass concentration of silk fibroin (e.g., high molecular weight silk fibroin) present in a silk fibroin composition that is no more than 2% (w/v or w/w), including, e.g., no more than 1% (w/v or w/w), or no more than 0.5% (w/v or w/w), of the volume or mass of the silk fibroin composition or silk fibroin article.

Higher concentrations of high molecular weight silk fibroin may also be desirable for use in some applications. As used herein, the term "higher concentrations of silk fibroin" can refer to concentrations of silk fibroin (e.g., high molecular weight silk fibroin) that are higher than the low concentrations as defined herein. The term "higher concentrations of silk fibroin" may refer to a mass concentration of silk fibroin (e.g., high molecular weight silk fibroin) present in a silk fibroin composition that is more than 1% (w/v or w/w), including, e.g., more than 2% (w/v or w/w), or more than 3% (w/v or w/w), or more than 4% (w/v or w/w), or more than 5% (w/v or w/w), or more than 6% (w/v or w/w), or more than 7% (w/v or w/w), or more than 8% (w/v or w/w), or more than 9% (w/v or w/w), of the volume or mass of the silk fibroin composition or silk fibroin article. For example, higher concentrations of high molecular weight silk fibroin can be used to yield a silk fibroin composition with enhanced mechanical properties and/or slower degradation rate. In these embodiments, the silk fibroin composition or silk fibroin article having a higher concentration of silk fibroin (e.g., high molecular weight silk fibroin) can have an elastic modulus of at least about 0.7 kPa or more, including, e.g., at least about 0.8 kPa, at least about 0.9 kPa, at least about 1 kPa, at least about 1.5 kPa, at least about 2 kPa, at least about 3 kPa, at least about 4 kPa, at least about 5 kPa, at least about 6 kPa, or higher. In some embodiments, the silk fibroin composition or silk fibroin article having a higher concentration of silk fibroin (e.g., high molecular weight silk fibroin) can have an elastic modulus of at least about 1 kPa, or at least about 2 kPa, or more.

The silk fibroin article compositions having a higher concentration of silk fibroin (e.g., high molecular weight silk fibroin) may have an ultimate tensile strength of at least about 20 kPa or more, including, e.g., at least about 30 kPa, at least about 40 kPa, at least about 50 kPa, at least about 60 kPa, at least about 70 kPa, at least about 80 kPa, at least about 90 kPa, at least about 100 kPa, at least about 200 kPa or higher. The silk fibroin composition or silk fibroin article having a higher concentration of silk fibroin (e.g., high molecular weight silk fibroin) may have an ultimate tensile strength of at least about 20 kPa or at least about 40 kPa, or at least about 80 kPa, or more.

An active agent and/or additive described herein may be added to the silk fibroin before further processing into a silk fibroin composition described herein. The active agent and/or additive may be dispersed homogeneously or heterogeneously within the silk fibroin, or dispersed in a gradient, e.g., using the modification method described in the U.S. Patent Application No. US 2007/0212730. Alternatively, the silk fibroin composition can be first formed and then contacted with (e.g., dipped into or incubated with) an active agent and/or additive. Alternatively or additionally, the at least one active agent and/or additive described herein can be coated on an exposed surface of the silk fibroin composition. Alternatively or additionally, the least one active agent and/or additive described here can diffuse into the silk fibroin composition.

Silk fibroin can be in a form selected from a film, a sheet, a gel or hydrogel, a mesh, a mat, a non-woven mat, a fabric, a scaffold, a tube, a slab or block, a fiber, a particle, powder, a 3-dimensional construct, an implant, a foam or a sponge, a needle, a lyophilized article, and any combinations thereof.

High molecular weight silk fibroin can be used to form a silk fibroin composition in any form. For example, the silk fibroin compositions can be present in a form selected from the group consisting of a film (See, e.g., U.S. Pat. Nos. 7,674,882; and 8,071,722); a sheet (see, e.g., PCT/US13/24744 filed Feb. 5, 2013); a gel (see, e.g., U.S. Pat. No. 8,187,616; and U.S. Pat. App. Nos. US 2012/0070427; and US 2011/0171239); a mesh or a mat (see, e.g., International Pat. App. No. WO 2011/008842); a non-woven mat or fabric (see, e.g., International Pat. App. Nos. WO 2003/043486 and WO 2004/080346); a scaffold (see, e.g., U.S. Pat. Nos. 7,842,780; and 8,361,617); a tube (see, e.g., U.S. Pat. App. No. US 2012/0123519; International Pat. App. No. WO 2009/126689; and International Pat. App. Serial No. PCT/US13/30206 filed Mar. 11, 2013); a slab or block; a fiber (see, e.g., U.S. Pat. App. No. US 2012/0244143); a high-density material (see, e.g., International Pat. App. Serial No. PCT/US13/35389 filed Apr. 5, 2013); a porous material such as a foam or sponge (see, e.g., U.S. Pat. Nos. 7,842,780; and 8,361,617); a coating (see, e.g., International Patent Application Nos. WO 2007/016524; WO 2012/145652); a machinable material (see, e.g., U.S. Prov. App. No. 61/808,768 filed Apr. 5, 2013); a powder; a lyophilized material; or any combinations thereof. The contents of each of the aforementioned patent applications are incorporated herein by reference in their entireties.

The silk fibroin composition may be formed as a film, e.g., a silk fibroin film. As used herein, the term "film" refers to a flat structure or a thin flexible substrate that can be rolled to form a tube. In some embodiments, the term "film" can also refer to a tubular flexible structure. It is to be noted that the term "film" is used in a generic sense to include a web, film, sheet, laminate, or the like. In some embodiments, the film can be a patterned film, e.g., nanopatterned film. Exemplary methods for preparing silk fibroin films are described in, for example, WO 2004/000915 and WO 2005/012606, content of both of which is incorporated herein by reference in its entirety. In some embodiments, a silk fibroin film can be produced by drying a silk fibroin solution on a substrate, e.g., a petri dish or a piece of acrylic. The resulting silk film can be further annealed, e.g., by water annealing or water vapor annealing, and then the resulting film can then be removed. The mechanical toughness of these films can allow them to be handled without film failure and rolled into a tight spiral.

The silk fibroin composition may be formed as a silk particle, e.g., a silk nanosphere or a silk microsphere. As used herein, the term "particle" includes spheres; rods; shells; and prisms; and these particles can be part of a network or an aggregate. Without limitations, the particle can have any size from nm to millimeters. As used herein, the term "microparticle" refers to a particle having a particle size of about 1 µm to about 1000 µm. As used herein, the term "nanoparticle" refers to particle having a particle size of about 0.1 nm to about 1000 nm. Particle size can greatly determine microscopic and macroscopic properties of the final product. Particle size is dependent on a number of process parameters, including the size of the ceramic balls used, the amount of silk placed in each ball mill cup, the rotational speed (RPM) of the machine, and the duration of ball milling. Particle size in the powder can be predicted based on some of these process parameters, e.g., with mathematical modeling and/or experimentation to determine the correlation. For example, this can be done by milling a given volume of silk fibroin for varying ball mill speeds and durations. Scanning Electron Microscopy (SEM) can be performed on representative samples from each experiment to determine particle size. Additional tests can be run on each sample to determine the effect of process parameters on the color, molecular weight, viscosity in a solution, and solubility in water of the resulting constructs.

Various methods of producing silk particles (e.g., nanoparticles and microparticles) are known in the art. In some embodiments, the silk particles can be produced by a polyvinyl alcohol (PVA) phase separation method as described in, e.g., International App. No. WO 2011/041395, the content of which is incorporated herein by reference in its entirety.

It may be desirable to have the silk fibroin composition to be porous. Too high porosity can generally yield a silk fibroin composition and thus the resulting network thereof with lower mechanical properties, but too low porosity can affect the release of an active agent embedded therein, if any. One of skill in the art can adjust the porosity accordingly, based on several factors such as desired release rates, molecular size and/or diffusion coefficient of the active agent, and/or concentrations and/or amounts of silk fibroin in a silk fibroin composition.

The porous silk fibroin composition can have any pore size. Methods for forming pores in a silk fibroin composition are known in the art and include, but are not limited, porogen-leaching methods, freeze-drying methods, and/or gas-forming method. Exemplary methods for forming pores in a silk-based material are described in U.S. Pat. App. Pub. Nos.: US 2010/0279112 and US 2010/0279112; and U.S. Pat. No. 7,842,780, all of which are incorporated herein by reference.

The silk fibroin may include an amphiphilic peptide, which possess both hydrophilic and hydrophobic properties. Amphiphilic molecules can generally interact with biological membranes by insertion of the hydrophobic part into the lipid membrane, while exposing the hydrophilic part to the aqueous environment.

After formation of the silk fibroin composition the silk fibroin can be further subjected to a post-treatment. A post-treatment can include any process that can alter a material or physical property of the silk fibroin composition. For example, the silk fibroin composition can be further processed into a variety of desired shapes. Examples of such processing methods include, but are not limited to, machining, turning (lathe), rolling, thread rolling, drilling, milling, sanding, punching, die cutting, blanking, broaching, and any combinations thereof.

The silk fibroin composition may be subjected to a post-treatment that can increase its mechanical performance. For example, in some embodiments, the silk fibroin composition, e.g., a film or a fiber can be further subjected to stretching or drawing over steam. The stretch or draw ratio (i.e., difference in length between before and after drawing divided by original length before drawing) can depend on the material property of the silk fibroin composition. Stretching or drawing the silk fibroin composition, e.g., a film, or a fiber, may provide additional alignment of silk fibroin molecules, and thus yield a stronger and more ductile silk fibroin material.

A post-treatment method may be applied to the silk fibroin composition to further induce a conformational change in the silk fibroin. A conformational change in the silk fibroin can increase crystallinity of the silk fibroin, e.g., silk II beta-sheet crystallinity. Inducing a conformational change in silk fibroin can facilitate formation of a solid-state silk fibroin composition and/or make the silk fibroin at least partially insoluble. Without wishing to be bound by a theory, in some embodiments, the induced conformational change can increase the crystallinity of the silk fibroin, e.g., silk II beta-sheet crystallinity, which can in turn modulate physical properties of silk fibroin (e.g., mechanical strength, degradability and/or solubility). Further, inducing formation of beta-sheet conformation structure in silk fibroin can prevent silk fibroin from contracting into a compact structure and/or forming an entanglement.

The silk fibroin composition described herein may be sterilized. Sterilization methods for biomaterials are well known in the art, including, but not limited to, gamma or ultraviolet radiation, autoclaving (e.g., heat/steam); alcohol sterilization (e.g., ethanol and methanol); and gas sterilization (e.g., ethylene oxide sterilization).

The silk fibroin can be modified for different applications and/or desired mechanical or chemical properties (e.g., to facilitate formation of a gradient of an additive (e.g., an active agent) in silk fibroin-based materials). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application No. US 2007/0212730), diazonium coupling reaction (see, e.g., U.S. Patent Application No. US 2009/0232963), avidin-biotin interaction (see, e.g., International Application No.: WO 2011/011347) and pegylation with chemically-active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein. Additionally, the silk fibroin-based material can be combined with a chemical, such as glycerol, that, e.g., affects flexibility of the material. See, e.g., WO 2010/042798, Modified Silk films Containing Glycerol. The contents of the aforementioned patent applications are all incorporated herein by reference.

In some embodiments, the silk fibroin solution and/or mat article can comprise at least one active agent. The active agent can be dispersed homogeneously or heterogeneously within silk fibroin, or dispersed in a gradient, e.g., using the carbodiimide-mediated modification method described in the U.S. Patent Application No. US 2007/0212730. In some embodiments, the active agent can be coated on a surface of the silk fibroin article, e.g., via diazonium coupling reaction (see, e.g., U.S. Patent Application No. US 2009/0232963), and/or avidin-biotin interaction (see, e.g., International Application No.: WO 2011/011347). Non-limiting examples of the active agent can include cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, therapeutic agents and prodrugs thereof, small molecules, and any combinations thereof. See, e.g., PCT Patent Publication No. WO/2012/145739 for compositions and methods for stabilization of at least one active agent with silk fibroin. In some embodiments, at least one active agent can be fused to silk fibroin to form a fusion protein. The contents of the aforementioned patent applications are incorporated herein by reference.

An especially useful active agent may be a "cerium oxide nanoparticle" (also referred to as "CeO2 nanoparticles," "nanoceria," or "CNPs"). The production of such cerium oxide nanoparticles has been described in, for example, Chigurupati, et al., Biomaterials 34(9):2194-2201 (2013); and U.S. Pat. No. 7,534,453, which is incorporated herein by reference. The CNPs may have a size range of about 2-10 nm, and in particular about 3-5 nm.

Another particularly useful active agent is stem cells, in particular mesenchymal stem cells. Stem cells have been shown to decrease inflammation and increase wound healing. The silk fibroin solution and mat of this disclosure can be effectively used to hold such stem cells in place on skin in need of such treatment, such as a wound, to enhance healing of the skin to which the stem cells are applied.

Another useful active agent is a microRNA (miR or miRNA), which are small noncoding RNA molecules involved in the posttranscriptional regulation of gene expression. miR regulate the inflammatory response at multiple levels. In particular, miR-146a acts as the "molecular brake" on the inflammatory response, by targeting and repressing the activation of the NFκB inflammatory pathway. Expression of miR-146a is significantly down-regulated in diabetic wounds and MSC correction of the wound healing impairment is associated with increased miR-146a expression and down-regulation of inflammatory cytokine production. Thus, silk fibroin compositions of this disclosure may comprise miR-146a attached to or imbedded within the silk fibroin compositions described herein. These miR-146a active agents may be further conjugated to the CNPs described above, such that the miR-146a-conjugated CNPs act as an active agent or therapeutic agent that is attached to, or incorporated in, the silk fibroin compositions of this disclosure.

Any amounts of an active agent can be present in or on the silk fibroin article. For example, in some embodiments, an active agent can be present in the silk fibroin composition or silk fibroin article at a concentration of about 0.001 wt % to about 50 wt %, about 0.005 wt % to about 40 wt %, about 0.01 wt % to about 30 wt %, about 0.05 wt % to about 20 wt %, about 0.1 wt % to about 10 wt %, or about 0.5 wt % to about 5 wt %.

The silk fibroin compositions may comprise one or more (e.g., one, two, three, four, five or more) additives. In some embodiments, the additive(s) can be incorporated into the silk fibroin. An additive can provide one or more desirable properties to the silk fibroin composition, e.g., strength, flexibility, ease of processing and handling, biocompatibility, bioresorbility, lack of air bubbles, surface morphology, and the like. The additive can be covalently or non-covalently linked with silk fibroin and/or can be integrated homogenously or heterogeneously within the silk fibroin-based material.

An additive may be selected from small organic or inorganic molecules; biocompatible polymers; plasticizers; small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. Furthermore, the additive can be in any physical form. For example, the additive can be in the form of a particle, a fiber, a film, a tube, a gel, a mesh, a mat, a non-woven mat, a powder, a liquid, or any combinations thereof. In some embodiments, the additive can be a particle (e.g., a microparticle or nanoparticle).

The total amount of additives in the silk fibroin composition may be in a range of about 0.1 wt % to about 0.99 wt % of the total silk fibroin in the composition.

The silk fibroin composition may comprise another silk material as an additive, for example, to produce a silk fibroin composite (e.g., 100% silk composite) with improved mechanical properties. Examples of silk materials that can be used as an additive include, without limitations, silk particles, silk fibers, silk micron-sized fibers, silk powder and unprocessed silk fibers. In some embodiments, the additive can be a silk particle or powder. Various methods of producing silk fibroin particles (e.g., nanoparticles and microparticles) are known in the art. In some embodiments, the silk particles can be produced by a polyvinyl alcohol (PVA) phase separation method as described in, e.g., International App. No. WO 2011/041395, the content of which is incorporated herein by reference in its entirety. Other methods for producing silk fibroin particles are described in U.S. App. Pub. No. U.S. 2010/0028451 and PCT App. Pub. No.: WO 2008/118133 (using lipid as a template for making silk microspheres or nanospheres), and in Wenk et al. J Control Release, Silk fibroin spheres as a platform for controlled drug delivery, 2008; 132: 26-34 (using spraying method to produce silk microspheres or nanospheres), content of all of which is incorporated herein by reference in its entirety.

Silk fibroin particles or powder may be obtained by inducing gelation in a silk fibroin solution and reducing the resulting silk fibroin gel into particles, e.g., by grinding, cutting, crushing, sieving, sifting, and/or filtering. Silk fibroin gels can be produced by sonicating a silk fibroin solution; applying a shear stress to the silk solution; modulating the salt content of the silk solution; and/or modulating the pH of the silk solution. The pH of the silk fibroin solution can be altered by subjecting the silk solution to an electric field and/or reducing the pH of the silk solution with an acid. Methods for producing silk gels using sonication are described in U.S. Pat. App. Pub No. U.S. 2010/0178304 and Int. Pat. App. Pub. No. WO 2008/150861, contents of both which are incorporated herein by reference in their entirety. Methods for producing silk fibroin gels using shear stress are described in International Patent App. Pub. No.: WO 2011/005381, the content of which is incorporated herein by reference in its entirety. Methods for producing silk fibroin gels by modulating the pH of the silk solution are described in U.S. Pat. App. Pub. No.: US 2011/0171239, the content of which is incorporated herein by reference in its entirety.

Silk fibroin particles can be produced using a freeze-drying method as described in U.S. Provisional Application Ser. No. 61/719,146, filed Oct. 26, 2012; and International Pat. App. No. PCT/US13/36356 filed: Apr. 12, 2013, content of each of which is incorporated herein by reference in its entirety. Specifically, a silk fibroin foam can be produced by freeze-drying a silk solution. The foam then can be reduced to particles. For example, a silk solution can be cooled to a temperature at which the liquid carrier transforms into a plurality of solid crystals or particles and removing at least some of the plurality of solid crystals or particles to leave a porous silk material (e.g., silk foam). After cooling, liquid carrier can be removed, at least partially, by sublimation, evaporation, and/or lyophilization. The liquid carrier can be removed under reduced pressure.

In some embodiments, no conformational change in the silk fibroin is induced, i.e., crystallinity of the silk fibroin is not altered or changed before subjecting the foam to particle formation.

After formation, the silk fibroin can be subjected to grinding, cutting, crushing, or any combinations thereof to form silk particles. For example, the silk fibroin can be blended in a conventional blender or milled in a ball mill to form silk particles of desired size.

Without limitations, the silk fibroin particles can be of any desired size. In some embodiments, the particles can have a size ranging from about 0.01 µm to about 1000 µm, about 0.05 µm to about 500 µm, about 0.1 µm to about 250 µm, about 0.25 µm to about 200 µm, or about 0.5 µm to about 100 µm. Further, the silk particle can be of any shape or form, e.g., spherical, rod, elliptical, cylindrical, capsule, or disc.

The silk fibroin particles can be a microparticle or a nanoparticle. In some embodiments, the silk particle can have a particle size of about 0.01 µm to about 1000 µm, about 0.05 µm to about 750 µm, about 0.1 µm to about 500 µm, about 0.25 µm to about 250 µm, or about 0.5 µm to about 100 µm. In some embodiments, the silk particle has a particle size of about 0.1 nm to about 1000 nm, about 0.5 nm to about 500 nm, about 1 nm to about 250 nm, about 10 nm to about 150 nm, or about 15 nm to about 100 nm.

The amount of the silk fibroin particles in the silk fibroin compositions can range from about 1% to about 99% (w/w or w/v) or can be from about 5% to about 95% (w/w or w/v), from about 10% to about 90% (w/w or w/v), from about 15% to about 80% (w/w or w/v), from about 20% to about 75% (w/w or w/v), from about 25% to about 60% (w/w or w/v), or from about 30% to about 50% (w/w or w/v).). The amount of the silk particles in the silk fibroin compositions can be less than 20%.

The silk fibers may be microfibers or nanofibers. The additive can be micron-sized silk fiber (10-600 µm). Micron-sized silk fibers can be obtained by hydrolyzing the degummed silk fibroin or by increasing the boing time of the degumming process. Alkali hydrolysis of silk fibroin to obtain micron-sized silk fibers is described in Mandal et al., PNAS, 2012, doi: 10.1073/pnas.1119474109; and PCT application no. PCT/US13/35389, filed Apr. 5, 2013, content of all of which is incorporated herein by reference. Because regenerated silk fibers made from HFIP silk solutions are mechanically strong, in some embodiments, the regenerated silk fibers can also be used as an additive.

The silk fiber can be an unprocessed silk fiber, e.g., raw silk or raw silk fiber. The term "raw silk" or "raw silk fiber" refers to silk fiber that has not been treated to remove sericin, and thus encompasses silk fibers taken directly from a cocoon. Thus, by unprocessed silk fiber is meant silk fibroin, obtained directly from the silk gland. When silk fibroin, obtained directly from the silk gland, is allowed to dry, the structure is referred to as silk I in the solid state. Thus, an unprocessed silk fiber comprises silk fibroin mostly in the silk I conformation. A regenerated or processed silk fiber on the other hand comprises silk fibroin having a substantial silk II or beta-sheet crystallinity.

The additive may also comprise at least one biocompatible polymer, including at least two biocompatible polymers, at least three biocompatible polymers, or more. For example, the silk fibroin compositions can comprise one or more biocompatible polymers in a total concentration of about 0.1 wt % to about 70 wt %, about 1 wt % to about 60 wt %, about 10 wt % to about 50 wt %, about 15 wt % to about 45 wt % or about 20 wt % to about 40 wt %. In some embodiments, the biocompatible polymer(s) can be incorporated homogenously or heterogeneously into the silk fibroin composition or silk fibroin article. In other embodiments, the biocompatible polymer(s) can be coated on a surface of the silk fibroin composition. The biocompatible polymer(s) can be covalently or non-covalently linked to silk fibroin in a silk fibroin composition. The biocompatible polymer(s) can be blended with silk fibroin within a silk fibroin composition. Examples of the biocompatible polymers can include non-degradable and/or biodegradable polymers, e.g., but are not limited to, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, other biocompatible and/or biodegradable polymers and any combinations thereof. See, e.g., International Application Nos.: WO 04/062697; WO 05/012606. The contents of the international patent applications are all incorporated herein by reference.

The biocompatible polymer may comprise PEG or PEO. As used herein, the term "polyethylene glycol" or "PEG" means an ethylene glycol polymer that contains about 20 to about 2000000 linked monomers, typically about 50-1000 linked monomers, usually about 100-300. PEG is also known as polyethylene oxide (PEO) or polyoxyethylene (POE), depending on its molecular weight. PEG, PEO, and POE are chemically synonymous, but PEG has previously tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete PEGs are also available with different geometries.

The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG With degradable linkages therein. Further, the PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented as R(-PEG-OH)m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as biocompatible polymers.

The additive can include an enzyme that hydrolyzes silk fibroin. Without wishing to be bound by theory, such enzymes can be used to control the degradation of the composition and/or silk fibroin composition.

The silk fibroin composition can have a porosity of at least about 1%, at least about 5%, at least about 10%, at least about 20%, at least about 30%, at least about 40%, at least about 50%, at least about 60%, at least about 70%, at least about 80%, at least about 90%, or higher. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The porous silk fibroin composition can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the pores of the silk fibroin composition can have a size distribution ranging from about 50 nm to about 1000 μm, from about 250 nm to about 500 μm, from about 500 nm to about 250 μm, from about 1 μm to about 200 μm, from about 10 μm to about 150 μm, or from about 50 μm to about 100 μm. In some embodiments, the silk fibroin composition can be swellable when hydrated. The sizes of the pores can then change depending on the water content in the silk matrix. In some embodiment, the pores can be filled with a fluid such as water or air.

Another aspect of this disclosure is a cosmetic or dermatological composition comprising a silk fibroin solution as described above and at least one cosmetic adjuvant chosen, for example, from fatty substances, glycosaminoglycans, extracellular matrix molecules, organic solvents, ionic and non-ionic thickeners, softeners, antioxidants, free-radical scavengers, opacifiers, stabilizers, emollients, silicones, alpha-hydroxy acids, insect repellents, antifoams, moisturizers, vitamins, fragrances, preserving agents, surfactants, fillers, polymers, propellants, acidifying and basifying agents, colorants and any other ingredient usually used in cosmetics and/or dermatology.

The fatty substances may comprise at least one ingredient chosen from oils and waxes. The term "oil" means a compound that is liquid at room temperature. The term "wax" means a compound that is solid or substantially solid at room temperature with a melting point that is generally greater than 35° C. The fatty substances further comprise fatty acids, fatty alcohols, and fatty acid esters, which may be linear or cyclic, such as benzoic, trimellitic, and hydroxybenzoic acid derivatives.

Oils may include mineral oils (paraffin), plant oils (sweet almond oil, macadamia oil, blackcurrant seed oil, jojoba oil), synthetic oils such as perhydrosqualene, fatty alcohols, fatty acids and fatty esters, octyl palmitate, isopropyl lanolate, and triglycerides including those of capric/caprylic acid), oxyethylenated or oxypropylenated fatty esters and ethers, silicone oils (cyclomethicone, polydimethylsiloxanes and PDMSs), fluoro oils, and polyalkylenes. Waxy compounds may include paraffin, carnauba wax, beeswax, and hydrogenated castor oil. Thickeners may include crosslinked polyacrylic acids, modified and unmodified guar gums, and celluloses, such as hydroxypropyl guar gum, methylhydroxyethylcellulose, and hydroxypropylmethylcellulose.

These cosmetic or dermatological compositions incorporating the silk fibroin solutions described herein may further include one or more active agent(s) as described herein. These cosmetic or dermatological compositions may therefore have a functional or therapeutic effect to skin to which they are applied, including a wound. In this aspect, these cosmetic or dermatological compositions may act as a topical delivery device for any of the active agents described herein to the skin of a mammal.

Silk Fibroin Mats

The silk fibroin compositions may be formed as a mat composed of silk fibroin fibers including woven or non-woven silk fibroin fibers. The mat may be an electrospun silk mat comprising silk fibroin, where the content of the silk fibroin protein in the silk mat ranges from about 50 wt % to about 90 wt %. The silk mat may have a thickness of about 20 to 80 microns, or may be as thin as about 20 to 30 microns. The electronspun silk mat may have interconnected pores with the pore throat size surface area averaging from about 0.1 to about 1 micron.

The electrospun silk mat may comprise silk fibroin protein as described above, and a polymeric material such as polyethylene glycol (PEG), and/or polyethylene oxide (PEO). The electrospun silk mat may have a silk fibroin protein/PEO blend ratio from 2:1 to 4:1, or silk percentage is about 75% w/w to 90% (w/w); and the silk mat has a thickness of about 20 to 80 about microns. Electrospun silk fibroin/PEO or silk fibroin/PEG mats demonstrate durable physical and bio-functional properties, such as fiber structure, topography, porosity, absorption, water vapor transmission rates, oxygen permeation, and biodegradability, relevant to biomaterial systems with utility for skin protection and strengthening.

Electro spinning is a simple, versatile, and useful technique for fabricating nanofibrous membranes from a rich variety of functional materials. Doshi & Reneker 35 J. Electro. 151-60 (1995); Reneker & Chun 7 Nanotech. 216-23 (1996); Fridrikh et al., 90 Phys. Rev. Let. 144502-06 (2003). Although a significant number of natural and synthetic materials have been electrospun to form wound dressings, challenges remain in terms of biocompatibility, mechanical properties, and overall functional performance. By continuously spinning silk fibroin to a targeted platform large, confluent silk mats are produced that are constructed of layered fiber sheets, with a thickness relative to the silk concentration and volume of spinning dope used. The silk mats may be immersed in methanol, triggering the physical crosslinking inducing the formation of water stabilized materials.

To produce silk blend mats, a PEO or PEG may be blended with an aqueous silk fibroin solution. The blended solution is electro spun to form a silk protein/polymer blended mat, which may be constraint-dried to form the final electrospun silk mat.

The electro spinning may be performed by any means known in the art (see, for example, U.S. Pat. No. 6,110,590). For example, a steel capillary tube with a 1.0 to 2.0 mm internal diameter tip is mounted on an adjustable, electrically insulated stand. The capillary tube is generally maintained at a high electric potential and mounted in the parallel plate geometry. The capillary tube may be connected to a syringe filled with silk/biocompatible polymer solution. A constant volume flow rate is usually maintained using a syringe pump, set to keep the solution at the tip of the tube without dripping.

After constraint drying, the electrospun mat may be treated in alcohol/water solution before or after the drying steps to induce the beta-sheet formation and crystallization. The alcohol may be methanol, ethanol, isopropyl alcohol (2-propanol) or n-butanol. Furthermore, the PEO or PEG may be extracted from the silk mat. Extraction of PEO or PEG from the silk mat may be performed by leaching the electrospun silk blend mats in water for a period of time, such as over 1 to 3 days.

The silk mat structure may enable the controlled release of an active agent from the silk mat fibers. For example, delivery of a therapeutic agent or biological material may be continuous from the silk mat to a topical site where treatment is needed, over hours, days or even several weeks.

The silk fibroin mat may be electrospun into a suitable sized mat for application to a small or large skin surface area.

The thickness of the electrospun silk mats is preferably from about 20 microns to about 80 microns. When a constraint-drying method is used, the thickness of the electrospun silk mats may average about 20 microns to 30 microns.

The fibers of the electrospun silk fibroin mats have a substantially uniform diameter distribution throughout the mat structure. These electrospun silk fibroin fibers may range from 200 nm to 500 nm in diameter that forms a dense mat structure.

"Constraint-drying technique" or "constraint-drying", as used herein, refers to the process where the silk material is dried while being constrained, such that it dries while undergoing a drawing force. For example, the constraining force may be attributed to the resultant contraction forces which occur as the silk material dries while attached over the mouth of a crystallization dish. These silk materials may be draped over and attached to the mouth of a crystallization dish. As water molecules evaporate, hydrophobic domains at the surface substrate and throughout the bulk region of the protein initiate the loss of free volume from the interstitial space of the non-woven cast and within bulk region of the material. The loss of free volume causes the material to contract and draw radially towards the rim of the crystallization dish. Attached to the rim of the crystallization dish, the material becomes constrained with the continuous loss of free volume and the fibers become aligned and elongated in the direction of the radial stress. Dependant on silk volume, if the material fibers contract beyond the elongation yield point, material shearing will occur at the material/crystallization dish rim surface interface. Contrary to the constrain-drying method, air-dried samples will continuously contract until dry into twisted, irregular conformations.

Constraint-drying may be performed with controlled evaporation. The method comprises taking electrospun silk/PEO blended mats from a water bath, draping the mats over a crystallization dish in a controlled humidity environment, for example, between 20% and 50% Relative Humidity until dry. An alternative method of constraint-drying employs a magnetic field to maintain a silk fibroin-based material being stretched until it becomes naturally or blown dry.

The conformation of the silk fibroin may be altered by water annealing. Temperature-controlled water vapor annealing (TCWVA) provides a simple and effective method to obtain refined control of the molecular structure of silk biomaterials. The silk materials can be prepared with control of crystallinity, from a low content using conditions at 4° C., to highest content of 60% crystallinity at 100° C.

Alteration in the conformation of the silk fibroin may be induced by immersing in alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is 100%. If the alteration in the conformation is by immersing in a solvent, the silk composition can be washed, e.g., with solvent/water gradient to remove any of the residual solvent that is used for the immersion.

Alternatively, the alteration in the conformation of the silk fibroin can be induced with shear stress (see, e.g., International Pat. App. No. WO/2011005381 which is incorporated herein by reference). The shear stress can be applied by passing the silk composition through a needle. Other methods of inducing conformational changes include applying an electric field, applying pressure, or changing the salt concentration.

After the treatment to induce the conformational change, silk fibroin in the silk composition can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, silk fibroin in the silk composition is present completely in a silk II beta-sheet conformation, i.e., 100% silk II beta-sheet crystallinity.

The electrospun silk fibroin mats prepared by these processes exhibit good structural, morphological, biofunctional and biocompatible properties suitable for application to skin to both protect and strengthen the skin.

The mat compositions of this disclosure can be fabricated by any other suitable method, including fiber spinning, solvent casting, injection molding, thermoforming, extrusion, sheet extrusion, blown film extrusion, compression molding, and the like. See, U.S. Pat. No. 8,173,163.

Besides mats, the above-described dissolved silk may also be fabricated into other forms, such as threads, fibers, foam, meshes, hydrogel, matrixes, three-dimensional scaffolds, tablets, filling material, tablet coating, microparticles, rods, nanoparticles, mats, etc. Methods for generating such are known in the art. See, e.g. U.S. Pat. No. 7,635,755, Altman, et al., Biomaterials 24:401, 2003; PCT Publications WO 2004/000915 and WO 2004/001103; and PCT Application No's PCT/US/04/111199 and PCT/US04/00255, which are herein incorporated by reference. Hydrogels can be prepared by methods known in the art. The sol-gel transition of the concentrated silk fibroin solution can be modified by changes in silk fibroin concentration, temperature, salt concentrations, pH, hydrophilic polymers, and the like. Before the sol-gel transition, the concentrated aqueous silk solution can be placed in a mold or form. The resulting hydrogel can then be cut into any shape, using a laser. See U.S. Patent Publication No. 2011/0008406.

Another aspect of this disclosure relates to articles of manufacture comprising one or more embodiments of the silk fibroin compositions described herein. Examples of articles of manufacture can include, but are not limited to, wound healing devices, topical reinforcement materials, and combinations thereof.

Methods of Protecting Skin or Enhancing the Strength of Skin

This disclosure provides methods of protecting skin or strengthening skin by applying silk fibroin solutions and mats to the skin of a mammal, thereby increasing the elastic modulus of the skin to which these silk fibroin materials are applied. In preferred methods, a silk fibroin solution is first applied topically to the skin, and thereafter, a silk fibroin mat is applied over the area to which the silk fibroin solution has been applied, to form a multi-layered skin protection/strengthening system. The silk fibroin can be used at any concentrations to impart desirable structural and/or mechanical properties to the skin to which it is applied. The silk fibroin can be provided as powder, which can be reconstituted in solution when it is ready for use, e.g., to apply to a wound.

In these methods, the silk fibroin can be used as a reinforcement material to the skin which enhance the mechanical properties (e.g., increased stiffness, increased elastic modulus, and/or increased tensile strength) of the skin.

In instances in which the silk fibroin compositions of this disclosure have been formed containing an active agent, the topical, layered silk fibroin system may act as a drug delivery device releasing the active agent to the skin to which the layered system is applied.

These methods of applying a solution of silk fibroin fibers to the skin of a mammal alone or in combination with the application of a silk fibroin mat over the silk solution to the skin may increase the elastic modulus of the skin of the mammal. These treatments may also increase the tensile strength of the skin of the mammal.

In instances in which the solution of silk fibroin fibers and/or silk fibroin mat is substantially free of sericin, the application to the skin may be hypoallergenic and thereby does not induce a clinically relevant or noticeable immune response in the mammal to which the silk fibroin composition(s) is applied.

In instances in which the solution of silk fibroin fibers and/or silk fibroin mat comprises any one of a biocompatible polymer selected from the group comprising polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, and combinations thereof, the treatment may further enhance other properties of the skin beyond tensile strength and/or increased elastic modulus.

In these methods, the composition of silk fibroin fibers may be applied as at least one of a spray, a liquid, a film, a foam, a suspension, a cream, an ointment, or a gel. The first application is preferably applied as a solution. This application may then be followed by application of a silk fibroin mat to further support and strengthen the initial silk fibroin application.

The silk fibroin mat may include a layer of an adhesive disposed on at least one surface of the mat to help locate and adhere the mat to the area to which silk fibroin solution had previously been applied.

In these methods, the mammal is preferably a human.

Complications of diabetes represent a significant clinical problem resulting in significant healthcare costs and patient morbidity. Diabetic wounds are one of the most common reasons for hospital admission and precede the majority of lower extremity amputations. Much research has been done to improve healing once a wound occurs; however, little has focused on molecular strategies for wound prevention. The inventors have previously shown that diabetic skin is biomechanically impaired due to lower collagen content which may make it more susceptible to injury. Therefore, the method of this disclosure may be used to apply silk fibroin compositions, including the layered application of a silk fibroin solution and a silk fibroin mat to the skin of a diabetic mammal, or an elderly mammal, to increase the biomechanical strength at baseline and thus decrease the susceptibility of weakened, esp. diabetic, skin to injury.

Thus, these methods of treatment or prevention may further comprise initially selecting a subject having Type 1 Diabetes, such as a subject who has been previously diagnosed with or identified as suffering from or having Type 1 Diabetes, or one or more complications related to Type 1 Diabetes, or a pre-diabetic condition, and optionally, but need not have already undergone treatment for the Type 1 Diabetes, the one or more complications related to Type 1 Diabetes, or the pre-diabetic condition. A subject can also be one who is not suffering from Type 1 Diabetes or a pre-diabetic condition. A subject can also be one who has been diagnosed with or identified as suffering from Type 1 Diabetes, one or more complications related to Type 1 Diabetes, or a pre-diabetic condition, but who show improvements in known Type 1 Diabetes risk factors as a result of receiving one or more treatments for Type 1 Diabetes, one or more complications related to Type 1 Diabetes, or the pre-diabetic condition. Alternatively, a subject can also be one who has not been previously diagnosed as having Type 1 Diabetes, one or more complications related to Type 1 Diabetes, or a pre-diabetic condition. For example, a subject can be one who exhibits one or more risk factors for Type 1 Diabetes, complications related to Type 1 Diabetes, or a pre-diabetic condition, or a subject who does not exhibit Type 1 Diabetes risk factors, or a subject who is asymptomatic for Type 1 Diabetes, one or more Type 1 Diabetes-related complications, or a pre-diabetic condition. A subject can also be one who is suffering from or at risk of developing Type 1 Diabetes or a pre-diabetic condition. A subject can also be one who has been diagnosed with or identified as having one or more complications related to Type 1 Diabetes or a pre-diabetic condition as defined herein, or alternatively, a subject can be one who has not been previously diagnosed with or identified as having one or more complications related to Type 1 Diabetes or a pre-diabetic condition.

These methods may be particularly useful in protecting an area of the skin from chaffing or from the formation of blisters following the application silk fibroin compositions, including the layered application of a silk fibroin solution and a silk fibroin mat, to the skin of the mammal, including diabetic mammals and/or elderly mammals.

These methods may be particularly useful in treating a blister by applying silk fibroin compositions, including the layered application of a silk fibroin solution and a silk fibroin mat, to a blister formed on the skin of the mammal, including the skin of diabetic mammals and/or elderly mammals.

These methods may be particularly useful in preventing injury to an area of the skin, by application of silk fibroin compositions, including the layered application of a silk fibroin solution and a silk fibroin mat, to the skin of the mammal, including diabetic mammals and/or elderly mammals, that is susceptible to injury. In these methods, the injury to the skin that is prevented or substantially reduced may be an acute injury or a repetitive stress injury.

As used herein, "prevention" or "preventing" of an injury or condition refers to reducing the occurrence of the injury or condition in a treated sample relative to an untreated control sample, or delay of the onset of one or more symptoms of the injury or condition relative to the untreated control sample.

As used herein, "wound" refers to an injury to any tissue, including but not limited to, acute, subacute, delayed or difficult to heal wounds, and chronic wounds. Examples of wounds may include both open and closed wounds. Wounds may include, for example, diabetic wounds or ulcers, burns, incisions, excisions, lacerations, abrasions, puncture or penetrating wounds, surgical wounds, contusions, hematomas, crushing injuries, and ulcers.

A "delayed" or "difficult to heal" wound may include, for example, a wound that is characterized at least in part by one or more of: 1) a prolonged inflammatory phase, 2) a slow forming extracellular matrix (ECM), and 3) a stalled or decreased rate of epithelialization. As used herein, a "chronic wound" may refer to, for example, a wound that is characterized at least in part by one or more of: 1) a chronic self-perpetuating state of wound inflammation, 2) a deficient and defective wound ECM, 3) poorly responding (senescent) wound cells especially fibroblasts, limiting ECM production, and 4) failure of re-epithelialization due in part to lack of the necessary ECM orchestration and lack of scaffold for migration. Chronic wounds include diabetic wounds or ulcers, venous ulcers, arterial ulcers, pressure ulcers, and vasculitic ulcers.

In addition, "wounds" may also include, for example, injuries to the skin and subcutaneous tissue initiated by, for example, pressure sores from extended bed rest and wounds induced by trauma, and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include pressure sores, venous stasis ulcers, and diabetic wounds or ulcers. The term "deep wound" is meant to include both Grade III and Grade IV wounds. A wound may be a wound as described above that is not a diabetic wound or ulcer.

The silk fibroin compositions of this disclosure may be used to treat wounds in a subject in need thereof by applying a silk fibroin composition, esp. a silk fibroin solution or mat of this disclosure, incorporating miR-146a conjugated to a CNP, as described above. Treatment of a diabetic wound with miR-146a conjugated to the CNPs incorporated within a silk fibroin composition of this disclosure can decrease the area of the diabetic wound, similar to the size of a non-diabetic wound at 3 and 10 days.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, it will be understood by those of ordinary skill in the art that any one of the various embodiments herein described and illustrated may be further modified to incorporate features shown in any of the other embodiments disclosed herein.

This disclosure is further illustrated by the following examples which should not be construed as limiting. The examples are illustrative only, and are not intended to limit, in any manner, any of the aspects described herein. The following examples do not in any way limit the invention.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Materials and Methods Used for Increasing the Biomechanical Strength of Mammalian Skin The inventors hypothesized that treatment of diabetic skin with silk fibroin would increase the biomechanical strength at baseline and thus decrease the susceptibility of diabetic skin to injury. To test this hypothesis, silk fibroin protein was isolated from the cocoons of *Bombyx mori* silk worm by removing sericin. The silk fibroin solution was used either directly or electro-spun to form a mat of silk fibroin nanofibers (SFMat). Skin from the back of 10 weeks old diabetic mice was treated with silk fibroin solution or silk fibroin+SFMat, or control, and biomechanical testing performed.

Example 2

Figure 2:
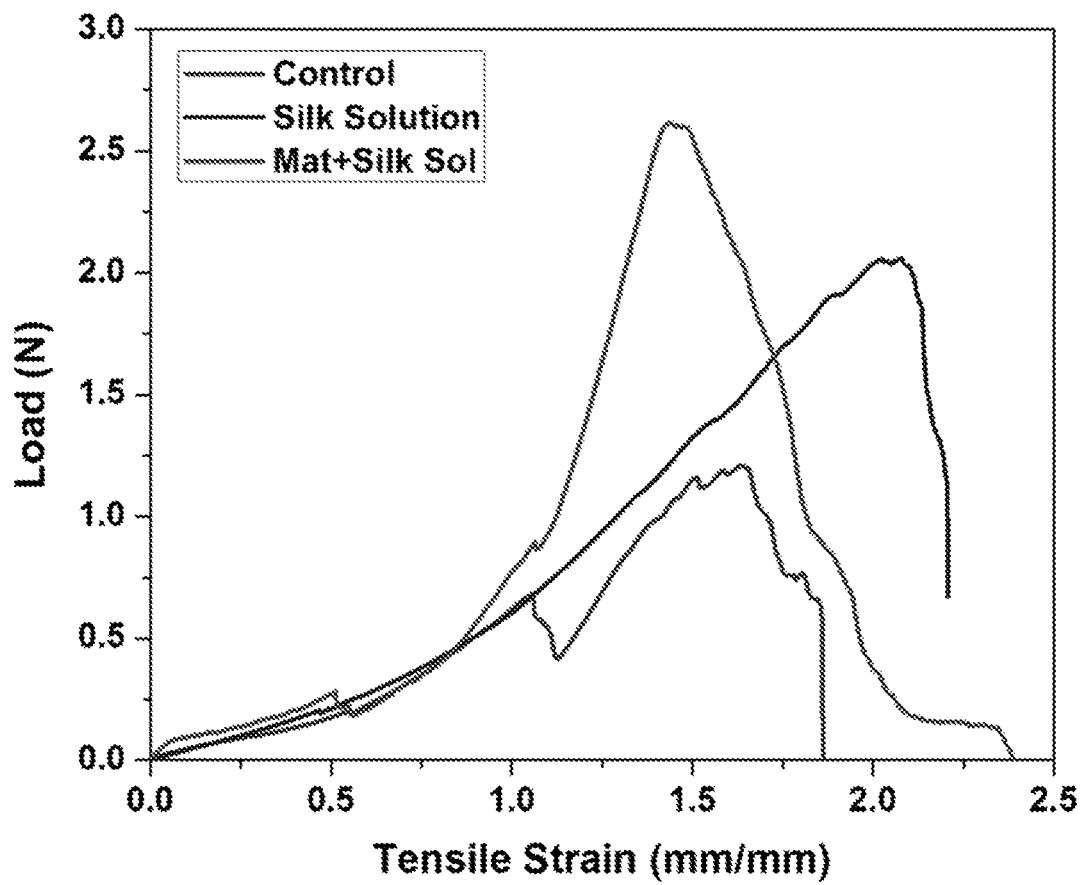
FIG. 2 shows the effect of treating mammalian skin with silk fibroin solution, or silk fibroin and silk fibroin mat on tensile strength of diabetic skin compared.

Testing Elastic Modulus and Tensile Strength of Mammalian Skin Treated with Silk Fibroin Treatment with silk fibroin solution, or silk fibroin+SFMat increased the elastic modulus (FIG. 1) and tensile strength (FIG. 2) of the diabetic skin compared to control. There was no significant difference between the tensile strength of Silk fibroin or Silk fibroin+SFMat treated skin, however silk fibroin solution+SFMat significantly increased the elastic modulus of diabetic skin compared to silk fibroin treatment alone (FIG. 1). The elastic modulus and tensile strength data is presented in the following table:

| Samples | Modulus (MPa) | Ultimate Tensile Strength(Mpa) |
|---|---|---|
| Control skin (db) | 0.1518 ± 0.0540 | 0.1372 ± 0.0228 |
| Silk solution spray on Skin | 0.1906 ± 0.0366 (7%) | 0.2095 ± 0.0052 (30%) |
| Silk solution + silk Mat on Skin | 0.5500 ± 0.0221 (72%) | 0.2496 ± 0.0171 (45%) |

These data demonstrate that the use of silk nanofibers can improve the biomechanical properties of skin at baseline, with increased tensile strength and increased modulus.

Example 3

Nanosilk is an Effective Delivery Method for CNP-146a

Complications of diabetes including peripheral neuropathy, increased bacterial load, and inferior biomechanical skin properties predispose diabetic skin to injury and chronic wound formation. As described above, the inventors tested multiple formulations of nanosilk, including a liquid and matte formulation, and showed that the nanosilk liquid improves biomechanical properties of human skin. Nanosilk liquid has also been used as a delivery method for cerium oxide nanoparticles ("nanoceria" or "CNPs"; the synthesis of which has been described in Chigurupati, et al., Biomaterials 34(9):2194-2201 (2013); and U.S. Pat. No. 7,534,453) conjugated to miRNA-146a ("CNP-146a", the detailed synthesis and characterization of which has been described in PCT Publication No. WO 2017/091700 with international filing date of 23 Nov. 2016, which is incorporated herein by reference). Briefly, oligonucleotides (i.e. miRNA-146a) contain phosphate groups carrying a negative charge along the chain that can electrostatically interact with the positively charged surface of the CNPs. In addition, oligonucleotides have hydroxyl groups of ribose and amino groups available for conjugation with the CNPs. The terminal functional group (amino, thiol, azide) for conjugation is also an option. Providing an appropriate excess of oligonucleotide in reaction medium (basically 10-15 molecules per nanoparticle), conjugation can be accomplished via different reactions. For example, amino groups of oligonucleotide can be coupled with CNP hydroxyl groups or functional groups of CNP coating after their activation with carbodiimide (CDI) or other bifunctional activating agent. Unbound compounds, as well as by-products, can be removed by centrifugation at 8000 g for 10 min and by dialysis against water or PBS using mini dialysis columns with at least 20 kDa cut off.

In this example, nanosilk was created from silk fibroin isolated from the cocoons of *Bombyx mori* silk worms, cut into small pieces, and dissolved in solution to obtain the viscosity needed for electrospinning nanofibers.

For biomechanical testing, human skin from diabetic patients was trimmed to uniform thickness and then cut into a standard dumbbell shape. 10 μL of either PBS or 7% nanosilk was applied to the skin and allowed to dry. Instron 5942 testing unit with Bluehill 3 Software was used for analysis. As compiled in the following data table, the human skin samples treated with 7% nanosilk showed improved strength with increased maximum load of 58.2N compared to 47.2N. Elastic modulus measures resistance deformity when stress is applied. These data show improved modulus with 7% nanosilk: 110.3 MPa compared to 103.3 MPa. Skin elasticity was also improved as evidenced by increased extension at break: 32.4 mm for silk fibroin and 27.9 mm for PBS.

| N = 6 in each group | Maximum Load (N) | Elastic Modulus (MPa) | Extension at Break (mm) |
|---|---|---|---|
| PBS Control | 47.2 | 103.3 | 27.9 |
| 7% Nanosilk solution | 58.2 | 110.3 | 32.4 |

Separately, 30 female, 12-week old mice breed homozygous diabetic (Db/Db) were also used to test the wound healing properties of the silk fibroin nanoparticles ("NF"). A single 8 mm wound was made on the dorsal neck skin of each mouse with a punch biopsy. The wounds were treated with one-time administration of phosphate buffered saline (control), or differing concentrations of silk nanofibers embedded with 10 μM cerium oxide nanoparticles ("NF+10 uM CNP") or embedded with 10 μM cerium oxide nanoparticles conjugated to miRNA-146a ("NF+10 uM CNP-miRNA146a"), at time of wounding (FIG. 3).

Figure 3:
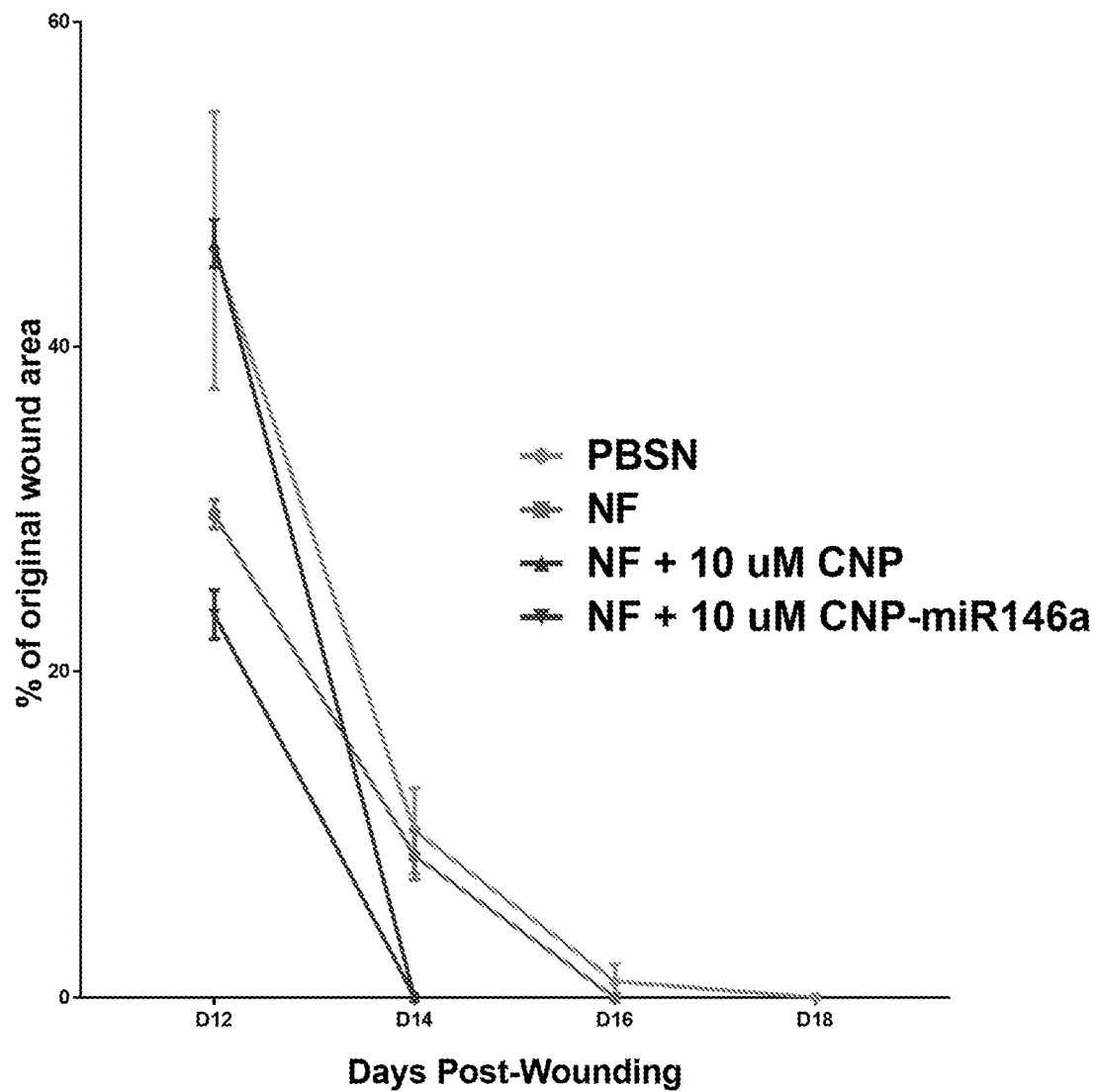

Diabetic mice treated with silk nanofibers embedded with CNP (with no conjugated miRNA-146a) showed improved wound healing, and the silk nanofibers embedded with CNP-miR146a enhanced diabetic wound healing (FIG. 3). Wounds healed at day 14 compared to day 18 for control diabetic mice (FIG. 3). Mice treated with 7% nanosilk liquid alone healed at day 16 (FIG. 3).

Figure 4:
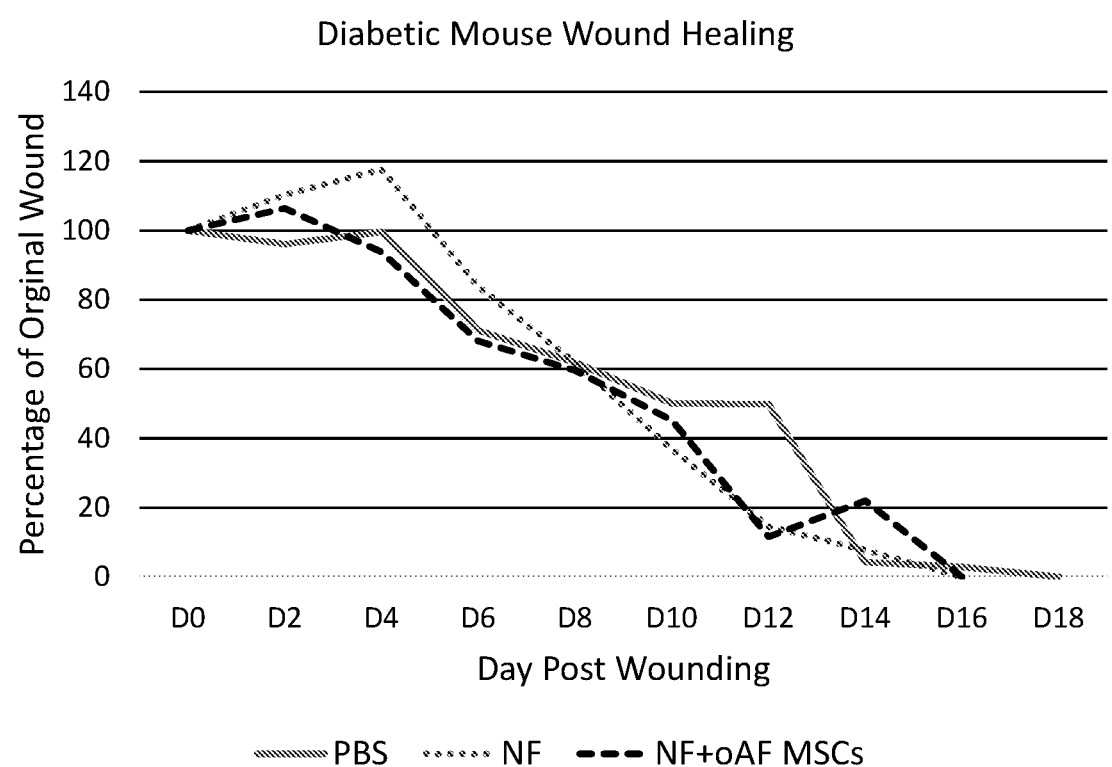
FIG. 4 shows a graph of a percent of original wound versus days post-wounding in diabetic mice showing effect of NF with or without ovine amniotic fluid mesenchymal stem cells.

Ovine amniotic fluid mesenchymal stem cells (oAF MSCs) were isolated from mid-gestation amniotic fluid collected during fetal intervention. oAF MSCs were cultured within a nanosilk matte for 7 days. Diabetic mice treated with silk nanofiber alone ("NF") had improved wound healing compared to control ("PBS") (day 16 compared to day 18) (FIG. 4). The application of silk nanofiber mats cultured with ovine amniotic stems cells ("NF+oAF MSCs") showed similar wound healing to the silk nanofiber alone (NF) (FIG. 4). In these studies, the silk nanofiber did not incorporate into the wound and acted as a biologic dressing that was shed as the wound healed.

These data demonstrate that the silk nanofiber improved skin strength, resilience, and elasticity of human skin to which it was applied. Thus, sild nanofiber presents an effective treatment to prevent injury to diabetic skin or improve healing once injury occurs. Additionally, it may be an ideal way to deliver other therapeutics (including mesenchymal stem cells and/or nanoceria, alone or conjugated to miRNA) to diabetic skin or wounds. For example, the nanofiber silk matte patch appears to hold mesenchymal stem cells stable in culture for several weeks and represents a stable and safe delivery method for these skin conditions.

In view of the many possible embodiments to which the principles of the disclosed compounds, compositions, and methods may be applied, it should be recognized that the foregoing description and examples are only preferred embodiments and should not be taken as limiting the scope of the invention.

What is claimed is:

1. A method of protecting skin of a mammal comprising:
    applying a solution of silk fibroin fibers to the skin of a mammal, wherein the mammal is non-diabetic and the skin is not damaged; and
    applying a silk fibroin mat over the solution of silk fibroin fibers applied to the skin of the mammal; thereby increasing the elastic modulus of the skin of the mammal.

2. The method of claim 1, wherein the silk fibroin fibers in the solution have a diameter in a range of about 1 to about 1,000 nm.

3. The method of claim 1, wherein the silk fibroin fibers in the solution are obtained from another solution containing a dissolved silkworm silk or a dissolved spider silk.

4. The method of claim 1, wherein the silk fibroin fibers in the solution have a sericin content of less than 5%.

5. The method of claim 1, wherein the silk fibroin fibers in the solution have a concentration of about 0.1 to about 25 weight percent of the solution.

6. The method of claim 1, wherein the solution of silk fibroin fibers is an aqueous solution or an alcohol solution.

7. The method of claim 1, wherein the solution of silk fibroin fibers further comprises a biocompatible polymer selected from the group comprising polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, and combinations thereof.

8. The method of claim 1, wherein the solution of silk fibroin fibers is applied as at least one of a spray, a liquid, a film, a foam, a suspension, a cream, an ointment, or a gel.

9. The method of claim 1, wherein the silk fibroin mat is applied as at least one of a sheet, a gel, a hydrogel, a mesh, a non-woven mat, a fabric, a scaffold, a tube, a slab, a fiber, a particle, a powder, a sponge, and a lyophilized article.

10. The method of claim 1, wherein the solution of silk fibroin fibers, the silk fibroin mat or both incorporates an active agent.

11. The method of claim 10, wherein the active agent is at least one of cerium oxide nanoparticle and mesenchymal stem cells.

12. The method of claim 11, wherein the cerium oxide nanoparticle is conjugated to a microRNA (miRNA).

13. The method of claim 12, wherein the miRNA is miRNA-146a.

* * * * *